United States Patent
Austin et al.

(10) Patent No.: US 12,420,704 B2
(45) Date of Patent: Sep. 23, 2025

(54) SYSTEMS AND METHODS TO DETERMINE AWAKENING LEAD TIME FOR WAKING UP SLEEPING DRIVER

(71) Applicant: Toyota Motor Engineering & Manufacturing North America, Inc., Plano, TX (US)

(72) Inventors: Benjamin Piya Austin, Saline, MI (US); John K. Lenneman, Okemos, MI (US); Joshua E. Domeyer, Madison, WI (US); Philip J. Babian, Canton, MI (US)

(73) Assignees: Toyota Motor Engineering & Manufacturing North America, Inc., Plano, TX (US); Toyota Jidosha Kabushiki Kaisha, Toyota (JP)

( * ) Notice: Subject to any disclaimer, the term of this patent is extended or adjusted under 35 U.S.C. 154(b) by 171 days.

(21) Appl. No.: 18/227,551

(22) Filed: Jul. 28, 2023

(65) Prior Publication Data
US 2025/0033559 A1    Jan. 30, 2025

(51) Int. Cl.
*B60Q 9/00* (2006.01)
*A61B 5/00* (2006.01)
*G08B 21/18* (2006.01)

(52) U.S. Cl.
CPC ............ *B60Q 9/00* (2013.01); *A61B 5/4809* (2013.01); *A61B 5/4812* (2013.01); *G08B 21/18* (2013.01); *A61B 2503/22* (2013.01)

(58) Field of Classification Search
CPC ....... B60Q 9/00; A61B 5/4809; A61B 5/4812; A61B 2503/22; A61B 5/18; G08B 21/18; G08B 21/06; B60W 50/14; B60W 2050/143; B60W 2050/146; B60W 60/0053
See application file for complete search history.

(56) References Cited

U.S. PATENT DOCUMENTS

| | | | |
|---|---|---|---|
| 9,340,204 B2 | 5/2016 | Schnieders et al. | |
| 11,137,760 B2 | 10/2021 | Latotzki et al. | |
| 2011/0022298 A1* | 1/2011 | Kronberg ............. | B60W 50/14 701/532 |
| 2020/0319635 A1 | 10/2020 | Andres et al. | |

(Continued)

FOREIGN PATENT DOCUMENTS

| | | |
|---|---|---|
| EP | 3691949 B1 | 10/2021 |
| JP | 2018149822 A | 9/2018 |

*Primary Examiner* — Ryan W Sherwin
(74) *Attorney, Agent, or Firm* — Dinsmore & Shohl LLP (57) ABSTRACT

Systems and methods providing sleep service in a vehicle to wake up a sleeping driver at a wake-up time based on the user profile of the driver are disclosed. In one embodiment, a sleeping service system includes a processor, a data receiver, an alarm, and a non-transitory memory module communicatively coupled to the processor, and a set of machine-readable instructions stored on the memory module that, when executed by the processor, cause the processor to perform operations. The operations include accessing a user profile of a driver, accessing a route information, calculating an action time based on one or more of upcoming events, calculating a current leading time based on the user profile, and providing a wake-up notification to the driver at a wake-up time based on the action time and the current leading-time period.

19 Claims, 5 Drawing Sheets

(56) References Cited

U.S. PATENT DOCUMENTS

| | | |
|---|---|---|
| 2021/0268902 A1 | 9/2021 | Kojima |
| 2021/0370984 A1* | 12/2021 | Alibeiginabi ............ G05D 1/81 |
| 2022/0203809 A1* | 6/2022 | Shimonomoto ......... A61B 5/16 |
| 2024/0317247 A1* | 9/2024 | Kaldobsky ............. G04G 13/02 |

* cited by examiner

SYSTEMS AND METHODS TO DETERMINE AWAKENING LEAD TIME FOR WAKING UP SLEEPING DRIVER

TECHNICAL FIELD

Embodiments described herein generally relate to systems and methods to determine awakening leading time to wake up a driver of an autonomous vehicle based on the driver's user profile.

BACKGROUND

Sleeping in the driver's seat becomes a possible scenario with the development of autonomous driving technology. A driver asleep within the vehicle may be woken up upon the vehicle system determining that a manual mode is desirable for the driver to control the vehicle. A driver upon awakening requires a period of take-over time to fully control the vehicle and thereby the vehicle system may determine a buffer period to wake up the driver before switching from autonomous mode to manual mode.

Individuals require different amounts of time to regain their conscious awareness after sleeping. One individual may take less time to exhibit a high level of cognitive performance due to one's healthy living style and psychological condition while another individual may take a longer time due to sleep deprivation, as examples. A leading time without considering the individuals' personal information may not meet each person's sleeping and waking needs in an autonomous driving trip.

Thus, personalized waking-up time systems and methods for awakening a driver based on personal user data may be desired in a vehicle providing sleeping service during an autonomous driving trip.

SUMMARY

In one embodiment, a sleeping service system includes a processor, a data receiver, an alarm, and a non-transitory memory module communicatively coupled to the processor, and a set of machine-readable instructions stored on the memory module that, when executed by the processor, cause the processor to perform operations. The operations include accessing a user profile of a driver, accessing a route information, calculating an action time based on one or a plurality of upcoming events, calculating a current leading time based on the user profile, and providing a wake-up notification to the driver at a wake-up time based on the action time and the current leading-time period.

In another embodiment, a method providing sleeping service in a vehicle includes accessing a user profile of a driver, accessing a route information, calculating an action time based on one or a plurality of upcoming events, calculating a current leading time based on the user profile, and providing a wake-up notification to the driver at a wake-up time based on the action time and the current leading-time period.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments of the present disclosure are directed to systems and methods for waking up a driver or other passengers of an autonomous vehicle at a particular time for the driver to take control of a vehicle. A driver should have situational awareness when manually operating a vehicle but may not need the same level of situational awareness once the vehicle begins to operate itself in an autonomous mode. During an autonomous mode, a vehicle may provide a sleeping service to a driver. However, once the vehicle is going to stop operating itself in an autonomous mode, the driver should regain situational awareness to appropriately operate the vehicle in a manual mode to secure a successful driving experience. Although a driver after awaking may take over the vehicle in tens of seconds, the driver may have not regained all the conscious awareness and reaction at the level that may be needed. In other words, in a vehicle providing a sleeping service to its drivers, it may be desired to have a system to provide a "buffer period" to allow the drivers to be able to regain a situational awareness that is comparable to that before they were asleep.

Various factors contribute to the impaired performance of a driver immediately after awakening. For example, a person tends to experience disorientation, and impaired cognitive performance right after awakening, especially when the awakening happens in the middle of rapid eye movement (REM) sleep. During this period, a phenomenon called "sleep inertia" or "waking up tired" occurs, and the person gradually regains conscious awareness and performance. However, in terms of controlling a vehicle during driving, the "waking up tired" period is undesirable and may have serious effects on the driver's attention, judgment, decision-making, coordination, vigilance, and reaction time. Other factors affecting driving performance immediately after awakening may include the driver's health condition, diet, and exercise habits, food and medication consumed shortly before driving, sleeping habits, driving habits, the time of the day when driving, environmental conditions, and the driver's psychological conditions before and during the driving. Each factor may contribute differently in determining how much time an individual needs to regain full situational awareness. Consequently, it is desirable to wake up each individual driver at a unique wake up time. As such, a sleeping service system can use a driver's individual wellness and activity information to calculate a leading-time period for a successful wake up of the driver.

As described in detail herein, embodiments of the present disclosure are directed to systems and methods for a personalized waking up service provided to a driver sleeping in a vehicle when the vehicle is switching its mode of operation from autonomous to manual control. Various embodiments of systems and methods for determining a leading-time period to awaken a driver based on a personal user profile with respect to vehicle mode switching are described in detail below.

Figure 1:
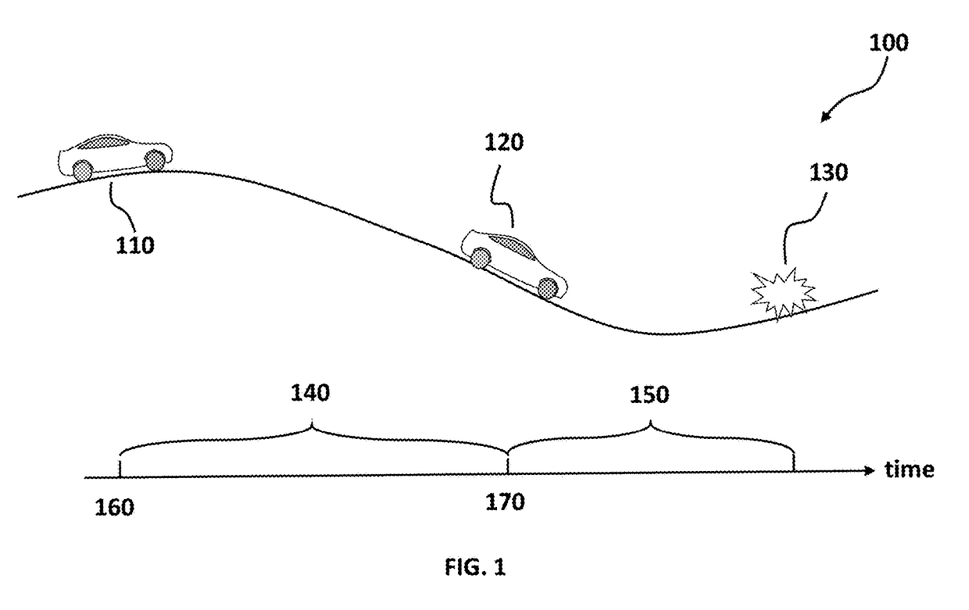
FIG. 1 schematically depicts an example 100 of a vehicle on a route at different points regarding switching from driver sleeping mode to manual control mode and the elapsed time between these points according to one or more embodiments illustrated and described herein.

Referring now to FIG. 1, an example vehicle driving in a route from a starting point A to a destination point B is provided. After the driver elects to use the sleeping service in autonomous driving, an autonomous driving system takes over driving during the driver's sleeping. A sleeping service system allows the driver to sleep and be free from the tasks of operations. During the driver's sleeping, there may be a need for the driver to manually operate the vehicle. With a given route, for example, entered or calculated by GPS systems, the sleeping service system may determine an incident point 130 based on the route, the route conditions, and traffic conditions, such that after reaching the incident point, the vehicle may not be desirable to continue traveling without a driver's precise control of the vehicle. One or more upcoming events in the route may happen at an incident point such that the driver's manual control is desirable. An incident point may be exits of highways, high traffic volume, accidents, weather conditions, and the like. The sleeping service system further calculates an action time 150, which is about how much time the individual driver needs to control the vehicle to take mitigating actions (such as reducing speed, changing lanes, or detouring) to reduce risks before encountering the incident point 130. Accordingly, an action point 120 at action time 170 in the route is calculated where the vehicle is about to reach the incident point 130 after an action-time period 150. A vehicle GPS system, for example, may dynamically update the route information and traffic information. Consequently, the sleeping service system dynamically updates the incident point 130 and the action point 120 according to the updated route information. It should be understood that the route information and traffic information may be entered or provided by other systems. It should also be understood that updated route information, traffic information, or other collected data from the sensors of the vehicle may instantly trigger a waking up alarm, decelerate or stop the vehicle, or pull over the vehicle to a pull-off location.

In some embodiments, in order for an awakening driver to regain full situational awareness at the action point 120, the driver is woken up at a wake-up time 160 when the vehicle travels to a waking-up point 110 in the route. The vehicle may not switch the operation from the autonomous mode to the manual mode around or before the action time 170 to allow the driver to take over. The sleeping service system calculates a current leading-time period 140 representing the traveling time between the wake-up time 160 at the wake-up point 110 and the action time 170 at the action point 120. The current leading-time period 140 may be long enough for the driver to regain full situational awareness without being affected under the "waking up tired" state. As such, the driver performance is not impaired at and after the action time 170 to adapt to the upcoming event at the incident point and thereafter. A leading-time period is a period for a driver to recover the situational awareness from the "waking up tired" state and other sleeping effects, calculated based on user profile. Various types of leading-time periods may be adopted to calculate the current leading-time period 140.

Figure 2:
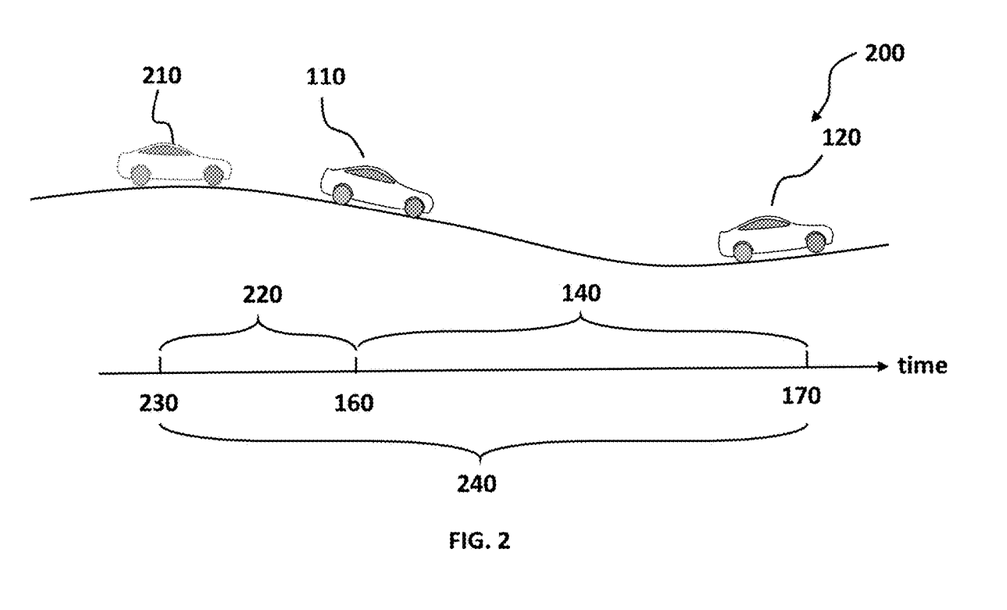
FIG. 2 schematically depicts another example 200 of a vehicle on a route at different points regarding switching from driver sleeping mode to manual control mode and the elapsed time between these points according to one or more embodiments illustrated and described herein.

Referring now to FIG. 2, an illustration of a sleeping service determining a leading-time period based on a driver's long-term user data is provided. In one embodiment, after the sleeping service system determines the incident point 130, the action point 120, and the action time 170, the system determines a base point 210 and a base leading time 230 based on the user profile of the driver. The period between base leading time 230 and action time 170 is the base leading-time period 240. The base leading-time period is calculated based on the user's historic data in the user profile. The base leading-time period reflects a user's long-term behaviors in determining the period for the user to recover from the "waking up tired," and is unique to each individual user. The current leading-time period for a driver to behave in accordance with the driver's long-term behaviors may be identical as the base leading-time period.

In some embodiments, after calculating a base leading-time period, a sleeping service system calculates a deviation leading-time period (see block 307 of FIG. 3) to determine the wake-up time 160 at the wake-up point 110. The deviation leading-time period may be a positive or negative value and the wake-up point may be closer or farther from the action point.

In some embodiments, after calculating a base leading-time period, a sleeping service system calculates an adjustment leading-time period 220 to determine the wake-up time 160 at the wake-up point 110. The adjustment leading-time period may be a positive or negative value and the wake-up point may be closer or farther from the action point.

In some embodiments, a sleeping service system may calculate both a deviation leading-time period and an adjustment leading-time period to determine the wake-up time 160 at the wake-up point 110. The combination of the deviation leading-time period and the adjustment leading-time period may be a positive or negative value and the wake-up point may be closer or farther from the action point.

In embodiments, the sleeping service system may work in coordination with the vehicle navigation system to optimize wake-up time 160 by selecting routes that allow the user to get through REM and other periods where the individual might experience grogginess after waking. For example, the user may decide to take a nap that is longer than the traveling time of the shortest route. The system may select a longer route for the user to finish the nap and wake up in a conscious state to control the vehicle.

Figure 3:
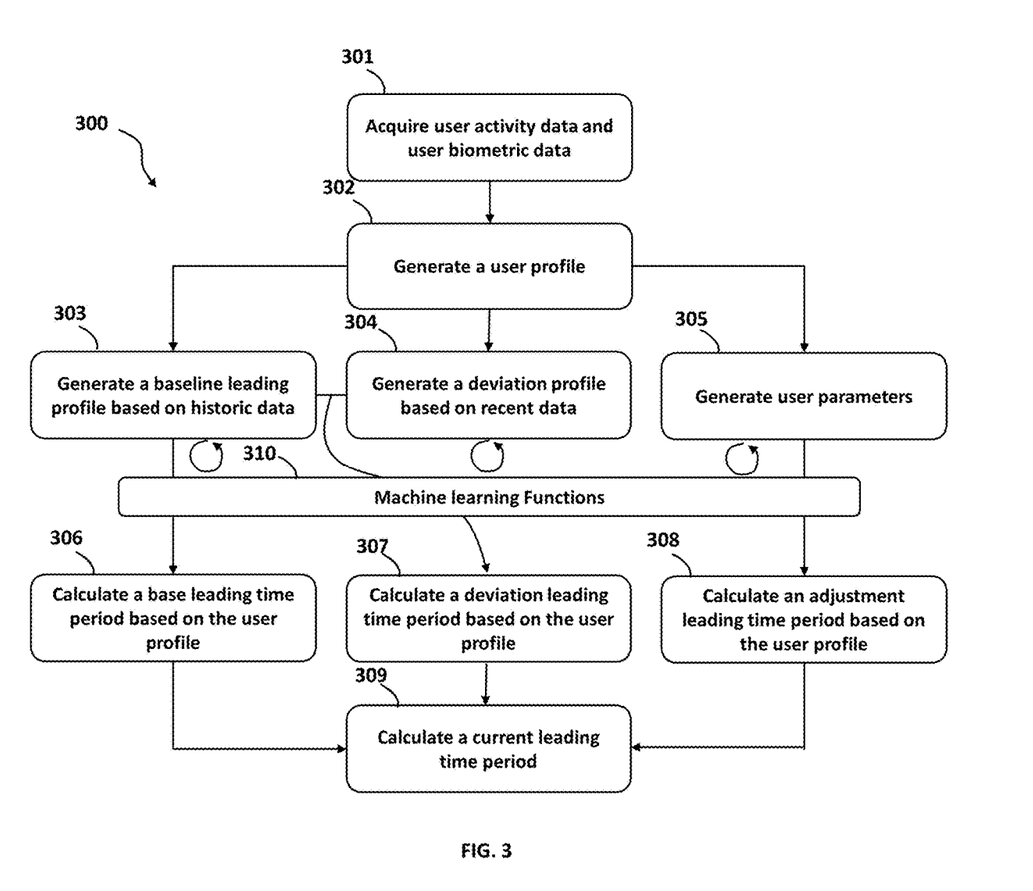
FIG. 3 graphically depicts a flowchart 300 of an example method for calculating a current leading-time period according to one or more embodiments illustrated and described herein.

Referring now to FIG. 3, a flowchart of an example method 300 for calculating a current leading-time period is depicted. It should be understood that embodiments are not limited by the order of the steps in flowchart 300 nor are embodiments limited to the steps included in flowchart 300.

At block 301, a sleeping service system determines one or more users who drive the vehicle and acquires their user activity data and user biometric data on a daily basis. The user activity data may include but is not limited to a user's physical activities, sleeping and waking data, diet, driving performance, or psychological status. The user biometric data may include, but is not limited to, vital signs selected from said driver's temperature, heart rate, blood pressure, oxygen saturation, and respiratory rate. The system may acquire the activity data or the user biometric data from one or more sources including, but not limited to, smart home servers, consumer electronics, automatic biometric monitoring technologies, or manual inputs. The system may use various data sources in determining a user's health conditions, sleeping wellness, and psychological status. For example, the system may find the user under a psychological stressing status based on the user's behaviors captured by home security cameras and the user's biometric data recorded by the user's smart watch.

At block 302, the sleeping service system generates a user profile based on the user activity data and user biometric data as acquired and collected. The user profile includes any derivative data generated from the user profile, such as the user's health conditions, sleeping wellness, or psychological status. The user profile includes both historic data and the recent data. The system generates a baseline leading profile based on historic data as shown in block 303. The system generates a deviation profile by comparing the recent data and the historic data as shown in block 304. For example, the deviation profile may include data that a user with regular sleeping behavior of around eight hours a day sleeps four hours a day in the past two days. In some embodiments, the deviation data may include any deviation from the historic data of user's physical activities, sleeping and waking data, diet, driving performance, or psychological status. In some embodiments, the deviation data may include a deviation of a user's historic data of temperature, heart rate, blood pressure, oxygen saturation, or respiratory rate. In yet another embodiment, the deviation data may include a deviation of a user's historic data of a user's health conditions, sleeping wellness, or psychological status.

At block 306, a sleeping service system calculates a base leading-time period 240 based on the historic data of the user profile. In determining a period leading-time period, the system may consider various information in the historic data of the user profile, such as user past sleep quality and length, daily hour of wakefulness and sleep, diet, exercises, health conditions, age, sex, psychological conditions, or driving habits.

At block 307, a sleeping service system calculates a deviation leading time period based on the user profile. The system may compare the baseline leading profile and the deviation profile in calculating the deviation leading-time period. The system may consider any deviation of the various information in the deviation profile from the corresponding information in the baseline leading profile, such as user past sleep quality and length, daily hour of wakefulness and sleep, diet, exercises, health conditions, age, sex, psychological conditions, or driving habits. The deviation leading-time period, either positive or negative, may add on top of the base leading-time period in determining a wake-up point and a wake-up time.

In some embodiments, the system continuously acquires user activity data and user biometric data to generate a dynamic baseline leading profile and a dynamic deviation profile. The system may adopt the dynamic profiles to modify and update the base leading-time period and the deviation leading-time period. In some embodiments, the sleeping service system may have machine learning functions by including a machine-learning module. The machine learning functions allow the system to dynamically calculate the base leading-time period and the deviation leading-time period and improve calculating accuracy. In the machine-learning module, new inputs, including daily user activity data and daily user biometric data may be provided to one or more artificial neural network (ANN) models as training data to continue to improve accuracy and minimize error of the ANN models. The user's data used to train and update the machine-learning module to estimate the optimum wake-up time may include the vehicle data right after the user's control over the vehicle after wake-up, such as lane deviation, longitudinal or speed consistency, steering wheel angle deviation, turn smoothness, turn signal timing, and the like. These vehicle data are used to indicate how well the driver is operating the vehicle after waking and help the system make more accurate estimations of when to wake the driver to optimize how well they are able to operate the vehicle. The one or more ANN models may utilize one to one, one to many, many to one, and/or many to many (e.g., sequence to sequence) sequence modeling. The machine-learning module may utilize one or more ANN models as understood to those skilled in the art or as yet-to-be-developed models to process natural language to be provided. Such ANN models may include artificial intelligence components selected from the group that may include, but not be limited to, an artificial intelligence engine, Bayesian inference engine, and a decision-making engine, and may have an adaptive learning engine further comprising a deep neural network learning engine. The one or more ANN models may employ a combination of artificial intelligence techniques, such as, but not limited to, Deep Learning, Random Forest Classifiers, Feature extraction from natural language input to the processing engine and/or the data map, audio, images, clustering algorithms, or combinations thereof.

In embodiments, a convolutional neural network (CNN) may be utilized. For example, a convolutional neural network (CNN) may be used as an ANN that, in a field of machine learning, for example, is a class of deep, feed-forward ANNs applied for adjuster assignment weights. CNNs may be shift or space invariant and utilize shared-weight architecture and translation invariance characteristics. Additionally or alternatively, a recurrent neural network (RNN) may be used as an ANN that is a feedback neural network. RNNs may use an internal memory state to process variable length sequences of inputs to generate one or more outputs. In RNNs, connections between nodes may form a Directed Acyclic Graph (DAG) along a temporal sequence. One or more different types of RNNs may be used such as a standard RNN, a Long Short Term Memory (LSTM) RNN architecture, and/or a Gated Recurrent Unit RNN architecture.

Referring back to FIG. 3, at block 305, a sleeping service system may generate user parameters from the user profile including, but not limited to, factors that may not be considered in the baseline leading profile and deviation profile. The parameters may be instant or most recent user activities and biometric parameters, including but not limited to, present sleeping status of the driver in the instant autonomous driving, wake-up planning, or food, drink and medication consumed shortly before driving. The sleeping status may include, but is not limited to, the driver's sleep depth, sleep phase, biological clock, or elapsed sleeping time.

Next, at block 308, a sleeping service system may calculate an adjustment leading-time period based on the user parameters. For example, a driver napping in the early stages of a sleeping cycle may not need an extra lead-time period while the system may calculate a positive adjustment leading-time period when the driver may awake at the fourth stage (the rapid eye movement, REM) of sleep. In embodiments, the system may use cameras to monitor the movements of the user's body and eyes during sleeping and physiological equipment to measure the user's body signals such as electroencephalography (EEG), electrooculography (EOG), and electromyography (EMG). The system may analyze the collected data from the cameras and the physiological equipment to determine the user's sleeping cycle, including whether the user is in the stage of REM. The analyzing results are further fed into the machine-learning module for validation of the calculated wake-up time 160 and increasing the accuracy of the machine-learning module. In one embodiment, the system calculates a low value of adjustment leading-time period when the system learns that the driver has a plan in waking up at or before reaching the wake-up point or the system learns the driver's cognitive activities reflecting her plan to wake up at or before reaching the wake-up point. In one embodiment, the system generates a zero or low value of adjustment leading-time period after learning that the driver consumes food, drink, or medication containing caffeine before taking the instant trip. In yet another embodiment, the system generates a high value of adjustment leading-time period after learning that the driver consumes food, drink, or medication affecting the driver's cognitive performance before taking the instant trip.

In block 309, a sleeping service system calculates a current leading-time period based on a base leading-time period, a deviation leading-time period, an adjustment leading-time period, or combination thereof. The system may use the current leading-time period to determine a wake-up time and a wake-up point based on a determined action time or a determined action point.

Figure 4:
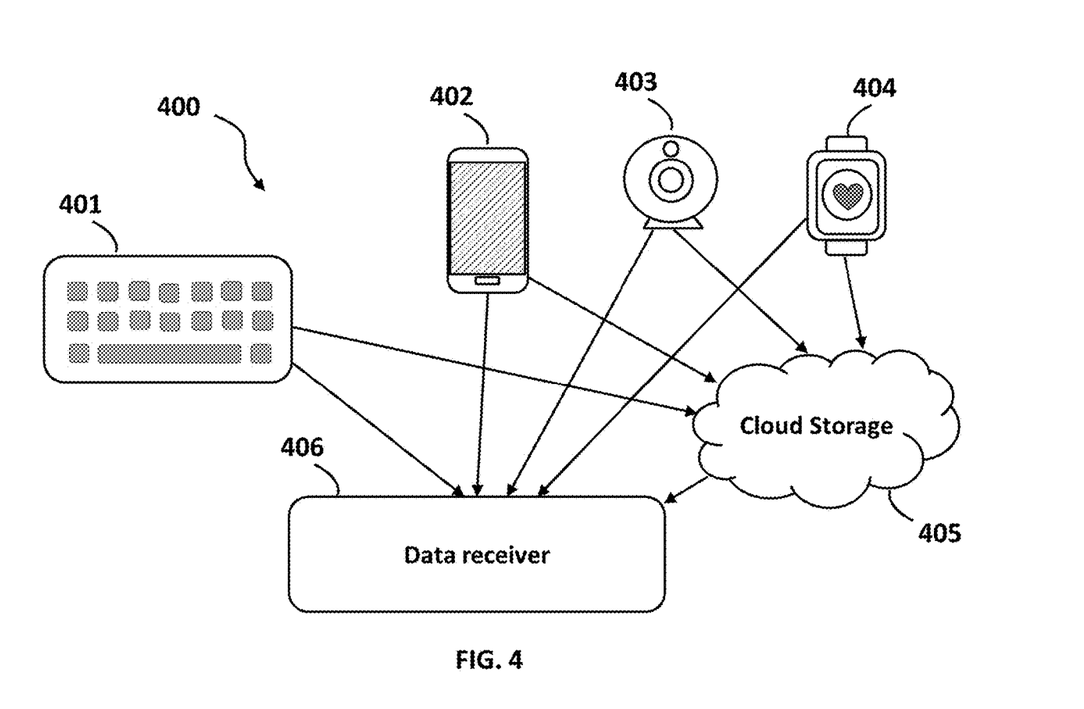
FIG. 4 schematically depicts a plurality of examples 400 for acquiring user activity data and user biometric data and communicating with a data receiver of the system according to one or more embodiments illustrated and described herein.

Referring to FIG. 4, examples of data collection by a sleeping service system is illustrated. The system may include a data receiver 406 to collect a driver's user activity data and user biometric data. The data receiver may receive data through automatic input or manual input 401. The sources of the data may include, but is not limited to, smart home servers, consumer electronics, or automatic biometric monitoring technologies. For example, videos captured by a home security camera or a webcam 403 may provide information of a user's daily activities at home; smart watches 404 and smart phones 402 may provide information of a user's daily biometric parameters and sleeping wellness. Occasionally, the data receiver may communicate with a cloud storage 405 to collect data that are transferred from sources mentioned above.

Figure 5:
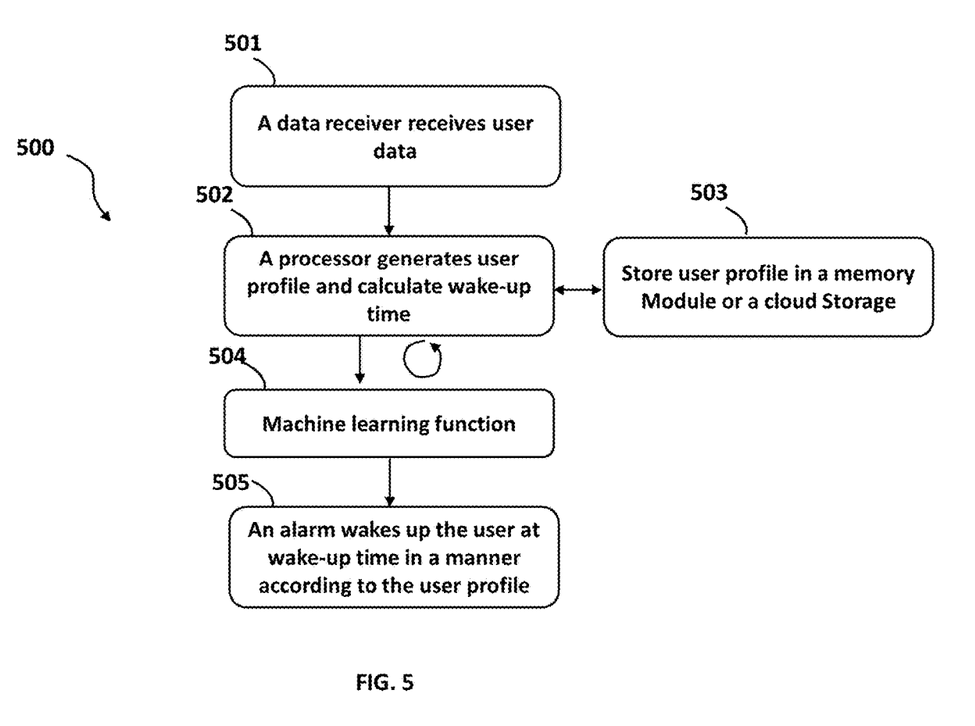
FIG. 5 graphically depicts a flowchart 500 of an example system for receiving user data, calculating a wake-up time, and waking up the driver using an alarm according to one or more embodiments illustrated and described herein.

Referring FIG. 5, an example sleeping system includes a data receiver 400, an alarm, a processor, and a memory. At block 501, the data receiver receives user activity data and user biometric data. Occasionally, the data receiver may receive data of user profile from external sources such as a cloud storage when the system stores the user profiles in the external sources. The data receiver then sends the user data and user profile to the processor.

Next, at block 502, the processor generates or updates a user profile based on the received user data. Further, based on the user profile, the processor calculates a current leading-time period and a wake-up time at a wake-up point in the route for a driver using the sleeping service. The processor may store the user profile in the memory or in external storage devices, such as a cloud storage, as in block 503.

At block 504, the processor may have a machine learning function to dynamically calculate and update the base leading-time period, the deviation leading-time period, or the adjustment leading-time period.

At block 505, the system has a wake-up function and provides a wake-up notification to the driver to wake up the user at the wake-up time. The notification may be an alarm. The wake-up function determines patterns, intensity, and means of the notifications based on the user profile. In embodiments, the means of the alarm may include, but is not limited to, sound, physical contact, light, or heat. In embodiments, the wake-up function may adopt machine learning functions in determining the patterns, intensity, and means of the alarm. In one embodiment, the alarm is installed in vehicle. In yet another embodiment, the alarm is installed in the driver's mobile device or in the passenger's mobile device.

In embodiments, the system may use clustering techniques to identify different sleep patterns of the user and create a personalized wake-up sequence that aligns with the user's sleep cycle. For example, the system may collect data on the user's sleep patterns using sensors such as wearable devices or mobile apps. The data may include metrics such as sleep duration, sleep stages, heart rate, movements and the like. The system may then use clustering techniques such as k-means or hierarchical clustering to group the sleep data into different clusters based on similarities in sleep patterns. The number and pattern of clusters may reflect the needs of wake-up to control the vehicle. For example, the system may define different wake-up patterns based on the clusters identified to recognize the user's consistent sleep pattern. For example, in one embodiment, a simple wake-up pattern of alarm that goes off at the same time each day is sufficient to wake up the user to handle the driving. In another embodiment, if a user is identified as having a varying sleep pattern, the wake-up pattern can be a gradually increasing alarm that aligns with the user's sleep cycle. As such, based on the user's cluster assignment, the system may select the appropriate wake-up pattern for the user and schedule the alarm based on the personalized wake-up pattern selected. In yet another embodiment, the system may adopt a Human-Machine Interface (HMI) to wake up a person using an alarm with a personalized wake-up pattern based on the user's profile. The system may deploy a mobile application that interfaces with the user's alarm clock or smart home device and allow the user to customize the wake-up pattern based on their sleep profile.

It should now be understood that embodiments of the present disclosure are directed to systems and methods for calculating an awakening leading-time for a driver sleeping during an autonomous driving. A representation of awakening time is calculated at a current leading-time period based on a user's personal activities and biometrics. A preferred wake-up time is calculated by factoring in the user's long-term and short-term activities and biometric data. Embodiments enable individualized awakening alarms to the user at the wake-up time. Embodiments further enable the personalized wake-up time and alarms being machine learned.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

It is noted that the terms "substantially" and "about" and "approximately" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A method of providing sleep service in a vehicle comprising:
   accessing a user profile of a driver, the user profile comprising user activity data and user biometric data;
   accessing route information;
   calculating an action time based on one or more upcoming events;
   calculating a current leading-time period based on the user profile;
   providing a wake-up notification to the driver at a wake-up time based on the action time and the current leading-time period; and
   wherein:
      the current leading-time period comprises a base leading-time period and a deviation leading-time period, and
      the deviation leading-time period is determined based on recent user activity data, recent user biometric data, historic user activity data, and historic user biometric data.

2. The method of claim 1, wherein the user activity data and the user biometric data are acquired from one or more of smart home servers, consumer electronics, automatic biometric monitoring technologies, and manual inputs.

3. The method of claim 1, wherein the user activity data comprise one or more of physical activities, sleeping and waking data, diet, driving performance, and psychological status.

4. The method of claim 1, wherein the user biometric data comprise one or more of vital signs comprising one or more of temperature, heart rate, blood pressure, oxygen saturation, and respiratory rate.

5. The method of claim 1, wherein the current leading-time period further comprises an adjustment leading-time period.

6. The method of claim 5, wherein one or more machine learning functions are applied to calculate the base leading-time period, the deviation leading-time period, and the adjustment leading-time period.

7. The method of claim 5, wherein the adjustment leading-time period is determined based on user parameters.

8. The method of claim 7, wherein the user parameters comprise one or more of information of present sleeping status of the driver, wake-up planning, and food intake, drink intake and medication intake before driving.

9. The method of claim 8, wherein the sleeping status comprises said driver's sleep depth, sleep phase, biological clock, and elapsed sleeping time.

10. The method of claim 1, wherein the base leading-time period is calculated based on a baseline leading profile comprising the historic user activity data and the historic user biometric data.

11. The method of claim 1, wherein the deviation leading-time period is generated by comparing the historic user activity data and the historic user biometric data with the recent user activity data and the user biometric data.

12. The method of claim 1, wherein the wake-up notification comprises an alarm to wake up the driver.

13. The method of claim 12, wherein:
   the alarm comprises sound, physical contact, light, or heat; and
   the alarm is determined by one or more of machine learning functions.

14. A system for providing sleep service in a vehicle comprising:
   a processor;
   a data receiver; an alarm;
   a non-transitory memory module communicatively coupled to the processor; and
   a set of machine-readable instructions stored on the memory module that, when executed by the processor, cause the processor to perform operations comprising:
      accessing a user profile of a driver, the user profile comprising user activity data and user biometric data;
      accessing route information;
      calculating an action time based on one or more upcoming events;
      calculating a current leading-time period based on the user profile;
      providing a wake-up notification to the driver at a wake-up time based on the action time and the current leading-time period; and
      wherein:
         the current leading-time period comprises a base leading-time period and a deviation leading-time period, and
         the deviation leading-time period is determined based on recent user activity data, recent user biometric data, historic user activity data, and historic user biometric data.

15. The system for providing sleep service in a vehicle of claim 14, wherein the data receiver acquires the user activity data and the user biometric data from one or more of smart home servers, consumer electronics, automatic biometric monitoring technologies, and manual inputs, and transfers the user activity data and the user biometric data to the processor.

16. The system for providing sleep service in a vehicle of claim 14, wherein the processor accesses the user activity data and the user biometric data and creates the user profile.

17. The system for providing sleep service in a vehicle of claim 14, wherein the user profile is stored locally in the memory module or remotely in a cloud storage.

18. The system for providing sleep service in a vehicle of claim 14, wherein:
   the alarm comprises sound, physical contact, light, or heat;
   and the alarm is determined by one or more machine learning functions.

19. The system for providing sleep service in a vehicle of claim 14, wherein the alarm is installed in the vehicle or in mobile devices taken with said driver or a non-driver in the vehicle.

* * * * *

UNITED STATES PATENT AND TRADEMARK OFFICE
CERTIFICATE OF CORRECTION

| | |
|---|---|
| PATENT NO. | : 12,420,704 B2 |
| APPLICATION NO. | : 18/227551 |
| DATED | : September 23, 2025 |
| INVENTOR(S) | : Benjamin Piya Austin et al. |

Page 1 of 1

It is certified that error appears in the above-identified patent and that said Letters Patent is hereby corrected as shown below:

On the Title Page

Item (73), assignees, delete "Toyota (JP)" and insert --Toyota-shi Aichi-ken (JP)--, therefor.

In the Specification

In Column 1, Line(s) 23, delete "amounts" and insert --amount--, therefor.

In Column 5, Line(s) 35, after "determining a", delete "period".

In the Claims

In Column 9, Line(s) 65, Claim 3, delete "comprise" and insert --comprises--, therefor.

In Column 10, Line(s) 2, Claim 4, delete "comprise" and insert --comprises--, therefor.

In Column 10, Line(s) 15, Claim 8, delete "comprise" and insert --comprises--, therefor.

Signed and Sealed this
Fourth Day of November, 2025

John A. Squires
*Director of the United States Patent and Trademark Office*